(12) United States Patent
El-Khouri et al.

(10) Patent No.: US 9,649,270 B2
(45) Date of Patent: *May 16, 2017

(54) COLOR COSMETIC COMPOSITIONS

(71) Applicant: L'Oréal, Paris (FR)

(72) Inventors: Rita Jaky El-Khouri, Morristown, NJ (US); Roshanak Debeaud, L'Haÿ-les-Roses (FR); Marco Vicic, Bry-sur-Marne (FR); Hy Si Bui, Piscataway, NJ (US)

(73) Assignee: L'Oréal, Paris (FR)

( * ) Notice: Subject to any disclaimer, the term of this patent is extended or adjusted under 35 U.S.C. 154(b) by 49 days.

This patent is subject to a terminal disclaimer.

(21) Appl. No.: 14/575,866

(22) Filed: Dec. 18, 2014

(65) Prior Publication Data
US 2016/0175232 A1    Jun. 23, 2016

(51) Int. Cl.
| | | |
|---|---|---|
| A61K 8/81 | (2006.01) | |
| A61K 8/891 | (2006.01) | |
| A61K 8/02 | (2006.01) | |
| A61K 8/362 | (2006.01) | |
| A61Q 1/06 | (2006.01) | |

(52) U.S. Cl.
CPC .......... *A61K 8/8152* (2013.01); *A61K 8/0241* (2013.01); *A61K 8/362* (2013.01); *A61K 8/891* (2013.01); *A61Q 1/06* (2013.01); *A61K 2800/412* (2013.01)

(58) Field of Classification Search
None
See application file for complete search history.

(56) References Cited

U.S. PATENT DOCUMENTS

| | | | |
|---|---|---|---|
| 5,851,517 A | 12/1998 | Mougin et al. | |
| 5,945,095 A | 8/1999 | Mougin et al. | |
| 2004/0137028 A1 | 7/2004 | de la Poterie | |
| 2006/0228314 A1* | 10/2006 | Patil ........................ | A61K 8/891 424/64 |
| 2007/0286824 A1* | 12/2007 | Rabe ........................ | A61K 8/11 424/59 |
| 2011/0243864 A1 | 10/2011 | Farcet et al. | |

FOREIGN PATENT DOCUMENTS

| | | |
|---|---|---|
| EP | 0 749 746 A1 | 12/1996 |
| EP | 0 749 747 A1 | 12/1996 |
| FR | 2 785 530 A1 | 5/2000 |
| FR | 2 937 645 A1 | 4/2010 |
| FR | 2 972 630 A1 | 9/2012 |
| FR | 2 972 631 A1 | 9/2012 |

OTHER PUBLICATIONS

Eva Snejdrova and Milan Dittrich (2012). Pharmaceutically Used Plasticizers, Recent Advances in Plasticizers, Dr. Mohammad Luqman (Ed.), ISBN: 978-953-51-0363-9, InTech, Available from: <http://www.intechopen.com/books/recent-advances-in-plasticizers/pharmaceutically-used-plasticizers>, p. 45-63.*
U.S. Appl. No. 14/575,259, filed Dec. 18, 2014, El-Khouri, et al.
French Preliminary Search Report and Written Opinion issued Sep. 9, 2014 in Patent Application No. 1362795 (with English translation of categories of cited documents).

* cited by examiner

*Primary Examiner* — Tracy Vivlemore
*Assistant Examiner* — Monica Shin
(74) *Attorney, Agent, or Firm* — Oblon, McClelland, Maier & Neustadt, L.L.P.

(57) ABSTRACT

Compositions containing at least one dispersion of acrylic polymer particles, at least one volatile oil, at least one coloring agent, at least one thickening agent, and at least about 15% by weight with respect to the weight of the composition of at least one plasticizing agent are provided.

16 Claims, No Drawings

COLOR COSMETIC COMPOSITIONS

FIELD OF THE INVENTION

The present invention relates to cosmetic compositions comprising at least one dispersion of acrylic polymer particles, at least one volatile oil, at least one coloring agent, at least one thickening agent, and at least about 15% by weight with respect to the weight of the composition of at least one plasticizing agent, as well as to methods for using and making such compositions.

DISCUSSION OF THE BACKGROUND

Many pigmented cosmetic compositions such as foundations and lipsticks have been developed for longer wear and transfer resistance properties. This is typically accomplished by the use of ingredients that form a film after application, ingredients such as silicone film forming agents. Such compositions generally contain volatile solvents which evaporate on contact with the skin, lips or other keratinous tissue, leaving behind a film or layer comprising waxes and/or resins, pigments, fillers, and actives.

In the past, it has been problematic to formulate such compositions which possess acceptable wear and transfer-resistance properties while at the same time having good feel, spreadability and stability properties.

Thus, there remains a need for improved cosmetic compositions, which have acceptable or improved wear, transfer-resistance, feel, spreadability and/or stability properties for application to keratin materials such as skin or lips.

Accordingly, one aspect of the present invention is to provide a care and/or makeup and/or treatment composition for keratinous material such as the skin or lips, which is able to address or overcome at least one of the aforementioned problems with the prior art compositions, as well as to provide methods for using and making such compositions.

SUMMARY OF THE INVENTION

The present invention relates to cosmetic compositions comprising at least one dispersion of acrylic polymer particles, at least one volatile oil, at least one coloring agent, at least one thickening agent, and at least about 15% by weight with respect to the weight of the composition of at least one plasticizing agent.

The present invention also relates to methods of treating, caring for and/or making up keratinous material (for example, skin or lips) by applying compositions of the present invention to the keratinous material in an amount sufficient to treat, care for and/or make up the keratinous material.

The present invention further relates to covering or hiding skin defects associated with keratinous material (for example, skin or lips) by applying compositions of the present invention to the keratinous material in an amount sufficient to cover or hide such skin defects.

The present invention also relates to methods of enhancing the appearance of keratinous material (for example, skin or lips) by applying compositions of the present invention to the keratinous material in an amount sufficient to enhance the appearance of the keratinous material.

The present invention further relates to compositions having improved cosmetic properties such as, for example, improved long wear, transfer resistance and/or waterproof properties, wherein the compositions comprise at least one dispersion of acrylic polymer particles, at least one volatile oil, at least one coloring agent, at least one thickening agent, and at least about 15% by weight with respect to the weight of the composition of at least one plasticizing agent.

The present invention also relates to methods of making a composition comprising combining at least one dispersion of acrylic polymer particles, at least one volatile oil, at least one coloring agent, at least one thickening agent, and at least about 15% by weight with respect to the weight of the composition of at least one plasticizing agent, and forming a cosmetic composition.

It is to be understood that both the foregoing general description and the following detailed description are exemplary and explanatory only, and are not restrictive of the invention.

DETAILED DESCRIPTION OF THE INVENTION

Other than in the operating examples, or where otherwise indicated, all numbers expressing quantities of ingredients and/or reaction conditions are to be understood as being modified in all instances by the term "about."

"Substituted" as used herein, means comprising at least one substituent. Non-limiting examples of substituents include atoms, such as oxygen atoms and nitrogen atoms, as well as functional groups, such as hydroxyl groups, ether groups, alkoxy groups, acyloxyalky groups, oxyalkylene groups, polyoxyalkylene groups, carboxylic acid groups, amine groups, acylamino groups, amide groups, halogen containing groups, ester groups, thiol groups, sulphonate groups, thiosulphate groups, siloxane groups, and polysiloxane groups. The substituent(s) may be further substituted.

"Volatile", as used herein, means having a flash point of less than about 100° C.

"Non-volatile", as used herein, means having a flash point of greater than about 100° C.

"Physiologically acceptable medium" is means a medium that is compatible with human keratin materials, for instance the skin, the lips, the nails, the eyelashes, the eyebrows or the hair.

"Cosmetic composition" means a composition that is compatible with keratin materials.

"Keratin materials" means the skin (body, face, contour of the eyes, scalp), head hair, eyelashes, eyebrows, bodily hairs, nails and/or lips.

"Film former" or "film forming agent" as used herein means a polymer that, after dissolution in at least one solvent, leaves a film on the substrate to which it is applied, for example, once the at least one solvent evaporates, absorbs and/or dissipates on the substrate.

"Transfer resistance" as used herein refers to the quality exhibited by compositions that are not readily removed by contact with another material, such as, for example, a glass, food, a kimwipe, an item of clothing or the skin, for example, when eating, drinking or wiping. Transfer resistance may be evaluated by any method known in the art for evaluating such. For example, transfer resistance of a composition may be evaluated by a "kiss" test. The "kiss" test may involve application of the composition to human lips followed by "kissing" a material, for example, a sheet of paper, after expiration of a certain amount of time following application, such as 2 minutes after application. Similarly, transfer resistance of a composition may be evaluated by the amount of product transferred or substrate (e.g., bioskin) from a wearer to any other substrate, such as transfer from the neck of an individual to a collar or transfer from bioskin to a kimwipe after the expiration of a certain amount of time following application. The amount of composition transferred to the substrate (e.g., collar, or paper) may then be evaluated and compared. For example, a composition may be transfer resistant if a majority of the product is left on the wearer, e.g., lips, neck, etc. Further, the amount transferred may be compared with that transferred by other compositions, such as commercially available compositions. "Transfer resistance" could also be determined via in-vitro methods using bioskin as known by those of ordinary skill in the art. For example, whether or not a composition is transfer-resistant could be determined by whether a composition does not transfer when applied onto a bioskin substrate and wiped with a kimwipe. In a preferred embodiment of the present invention, little or no composition is transferred to the substrate. Thus, transfer-resistant compositions include transfer-free compositions.

"Long wear" compositions as used herein, refers to compositions where at least one property chosen from consistency, texture, and color remains the same as at the time of application, as viewed by the naked eye, after an extended period of time, such as, for example, 1 hour, 2 hours, and further such as 8 hours. Long wear properties may be evaluated by any method known in the art for evaluating such properties. For example, long wear may be evaluated by a test involving the application of a composition to human skin (or lips) or bioskin and evaluating the consistency, texture and color of the composition after an extended period of time, or after exposure to rubbing and/or oil. For example, the consistency, texture and color of a lip composition may be evaluated immediately following application and these characteristics may then be re-evaluated and compared after an individual has worn the lip composition for a certain amount of time. Further, these characteristics may be evaluated with respect to other compositions, such as commercially available compositions. Examples of such methods are set forth in the examples of the present application in which commercial products are compared with the invention compositions, and in which testing is performed in vivo as well as on bioskin.

"Make-up composition" as used herein means any composition applied to keratin materials for aesthetic purposes. Examples of acceptable make-up compositions include, but are not limited to, lip compositions such as lipsticks and stick foundations.

The compositions and methods of the present invention can comprise, consist of, or consist essentially of the essential elements and limitations of the invention described herein, as well as any additional or optional ingredients, components, or limitations described herein or otherwise useful in personal care compositions intended for topical application to keratin materials.

The compositions of the present invention may be in any form. They may be an emulsion, such as an oil-in-water or water-in-oil emulsion, a multiple emulsion, such as an oil-in-water-in-oil emulsion or a water-in-oil-in-water emulsion, or a solid gel, including anhydrous gels. The compositions can also be in a form chosen from a translucent anhydrous gel and a transparent anhydrous gel. The compositions of the invention may, for example, comprise an external or continuous fatty phase. The compositions of the invention may be transparent or clear. The compositions can also be a molded composition or cast as a stick or a dish. The compositions can be a solid such as a molded stick or a poured stick. The composition can contain water, but it also may be anhydrous, if desired.

The compositions of the present invention are preferably anhydrous (that is, contain 2% or less of water, preferably contain 1% or less of water, and preferably contain 0% water).

According to an embodiment of the present invention, the compositions of the present invention are solid, where the solid nature of the compositions can be determined by determining the hardness of the compositions.

According to an embodiment of the present invention, the compositions of the present invention are not solid. For example the compositions are liquid. Examples of such non-solid compositions are liquid foundations as well as liquid lip compositions such as those applied with a finger or an applicator (wand).

Dispersion of Acrylic Polymer Particles

According to the present invention, compositions containing at least one dispersion of acrylic polymer particles are provided. According to the present invention, the dispersions of acrylic polymer particles are dispersions of C1-C4 alkyl(meth)acrylate polymer particles stabilized with stabilizers based on isobornyl(meth)acrylate polymer in a hydrocarbon-based oil. The dispersion of acrylic polymer particles has been previously disclosed in PCT patent application serial no. PCT/EP2014/07800, the entire contents of which is hereby incorporated by reference.

According to preferred embodiments, the polymer of the particles is a C1-C4 alkyl(meth)acrylate polymer. The C1-C4 alkyl(meth)acrylate monomers may be chosen from methyl(meth)acrylate, ethyl(meth)acrylate, n-propyl(meth) acrylate, isopropyl (meth)acrylate, n-butyl(meth)acrylate and tert-butyl(meth)acrylate. Preferably, the monomer is a C1-C4 alkyl acrylate monomer. Preferably, the polymer of the particles is a methyl acrylate and/or ethyl acrylate polymer.

The polymer of the particles may also comprise an ethylenically unsaturated acid monomer or the anhydride thereof, chosen preferably from ethylenically unsaturated acid monomers comprising at least one carboxylic, phosphoric or sulfonic acid function, such as, for example, crotonic acid, itaconic acid, fumaric acid, maleic acid, maleic anhydride, styrenesulfonic acid, vinylbenzoic acid, vinylphosphoric acid, acrylic acid, methacrylic acid, acrylamidopropanesulfonic acid or acrylamidoglycolic acid, and/or salts thereof. Preferably, the ethylenically unsaturated acid monomer is chosen from (meth)acrylic acid, maleic acid and maleic anhydride. The salts may preferably be chosen from salts of alkali metals, for example sodium or potassium; salts of alkaline-earth metals, for example calcium, magnesium or strontium; metal salts, for example zinc, aluminium, manganese or copper; ammonium salts of formula NH4+; quaternary ammonium salts; salts of organic amines, for instance salts of methylamine, dimethylamine, trimethylamine, triethylamine, ethylamine, 2-hydroxyethyl-amine, bis(2-hydroxyethyl)amine or tris(2-hydroxyethyl) amine; lysine or arginine salts.

The polymer of the particles may thus comprise or consist essentially of 80% to 100% by weight of C1-C4 alkyl(meth) acrylate and of 0 to 20% by weight of ethylenically unsaturated acid monomer, relative to the total weight of the polymer.

According to preferred embodiments, the polymer consists essentially of a polymer of one or more C1-C4 alkyl (meth)acrylate monomers.

According to preferred embodiments, the polymer consists essentially of a copolymer of C1-C4 (meth)acrylate and of (meth)acrylic acid or maleic anhydride.

The polymer of the particles may be chosen from, for example: methyl acrylate homopolymers; ethyl acrylate homopolymers; methyl acrylate/ethyl acrylate copolymers; methyl acrylate/ethyl acrylate/acrylic acid copolymers; methyl acrylate/ethyl acrylate/maleic anhydride copolymers; methyl acrylate/acrylic acid copolymers ethyl acrylate/acrylic acid copolymers; methyl acrylate/maleic anhydride copolymers; and ethyl acrylate/maleic anhydride copolymers.

Preferably, the polymer of the particles is a non-crosslinked polymer.

The polymer of the particles of the dispersion preferably has a number-average molecular weight ranging from about 2000 to about 10,000,000, preferably ranging from about 150,000 to 500,000, including all ranges and subranges therebetween.

The polymer of the particles are preferably present in the dispersion in a content ranging from about 21% to about 58.5% by weight, preferably ranging from about 36% to about 42% by weight, relative to the total weight of the dispersion, including all ranges and subranges therebetween.

The stabilizer is preferably an isobornyl(meth)acrylate polymer chosen from isobornyl(meth)acrylate homopolymer and statistical copolymers of isobornyl(meth)acrylate and of C1-C4 alkyl(meth)acrylate present in an isobornyl (meth)acrylate/C1-C4 alkyl(meth)acrylate weight ratio of greater than 4. Preferably, the weight ratio ranges from about 4.5 to about 19, including all ranges and subranges therebetween.

Preferably, the stabilizer is chosen from, for example: isobornyl acrylate homopolymers; statistical copolymers of isobornyl acrylate/methyl acrylate; statistical copolymers of isobornyl acrylate/methyl acrylate/ethyl acrylate; statistical copolymers of isobornyl methacrylate/methyl acrylate, in the weight ratio described previously.

The stabilizing polymer preferably has a number-average molecular weight ranging from about 10,000 to about 400,000, preferably ranging from about 20,000 to about 200,000, including all ranges and subranges therebetween.

Although not wishing to be bound by any particular theory, it is believed that the stabilizer is in contact with the surface of the polymer particles and thus makes it possible to stabilize these particles at the surface in order to keep these particles in dispersion in the non-aqueous medium of the dispersion.

Preferably, the combination of the stabilizer+polymer of the particles present in the dispersion comprises from about 10% to about 50% by weight of polymerized isobornyl (meth)acrylate, and from about 50% to about 90% by weight of polymerized C1-C4 alkyl (meth)acrylate, relative to the total weight of the combination of the stabilizer+polymer of the particles.

Preferably, the combination of the stabilizer+polymer of the particles present in the dispersion comprises from about 15% to about 30% by weight of polymerized isobornyl (meth)acrylate, and from about 70% to about 85% by weight of polymerized C1-C4 alkyl(meth)acrylate, relative to the total weight of the combination of the stabilizer+polymer of the particles.

The oily medium of the polymer dispersion comprises a hydrocarbon-based oil. The hydrocarbon-based oil is an oil that is liquid at room temperature (25° C.).

The term "hydrocarbon-based oil" means an oil formed essentially from, or even consisting of, carbon and hydrogen atoms, and optionally oxygen and nitrogen atoms, and not containing any silicon or fluorine atoms. It may contain, for example, alcohol, ester, ether, carboxylic acid, amine and/or amide groups.

The hydrocarbon-based oil may be chosen from, for example:

hydrocarbon-based oils containing from 8 to 14 carbon atoms, preferably:
  branched C8-C14 alkanes, for instance C8-C14 isoalkanes of petroleum origin (also known as isoparaffins), for instance isododecane (also known as 2,2,4,4,6-pentamethylheptane), isodecane and, for example, the oils sold under the trade name Isopar or Permethyl,
  linear alkanes, for instance n-dodecane (C12) and n-tetradecane (C14) sold by Sasol under the respective references Parafol 12-97 and Parafol 14-97, and also mixtures thereof, the undecane-tridecane mixture, the mixtures of n-undecane (C11) and of n-tridecane (C13) obtained in Examples 1 and 2 of patent application WO 2008/155 059 from the company Cognis, the disclosure of which is hereby incorporated by reference, and mixtures thereof, short-chain esters (containing from 3 to 8 carbon atoms in total) such as ethyl acetate, methyl acetate, propyl acetate or n-butyl acetate, hydrocarbon-based oils of plant origin such as triglycerides consisting of fatty acid esters of glycerol, the fatty acids of which may have chain lengths varying from C4 to C24, these chains possibly being linear or branched, and saturated or unsaturated; these oils are especially heptanoic or octanoic acid triglycerides, or alternatively wheatgerm oil, sunflower oil, grapeseed oil, sesame seed oil, corn oil, apricot oil, castor oil, shea oil, avocado oil, olive oil, soybean oil, sweet almond oil, palm oil, rapeseed oil, cottonseed oil, hazelnut oil, macadamia oil, jojoba oil, alfalfa oil, poppy oil, pumpkin oil, marrow oil, blackcurrant oil, evening primrose oil, millet oil, barley oil, quinoa oil, rye oil, safflower oil, candlenut oil, passion-flower oil and musk rose oil; shea butter; or else caprylic/capric acid triglycerides, for instance those sold by the company Stéarineries Dubois or those sold under the names Miglyol 810®, 812® and 818® by the company Dynamit Nobel, synthetic ethers containing from 10 to 40 carbon atoms;

linear or branched hydrocarbons of mineral or synthetic origin, such as petroleum jelly, polydecenes, hydrogenated polyisobutene such as Parleam®, squalane and liquid paraffins, and mixtures thereof, synthetic esters such as oils of formula R1COOR2 in which R1 represents a linear or branched fatty acid residue containing from 1 to 40 carbon atoms and R2 represents an, in particular, branched hydrocarbon-based chain containing from 1 to 40 carbon atoms, on condition that R1+R2≥10, for instance purcellin oil (cetostearyl octanoate), isopropyl myristate, isopropyl palmitate, C12 to C15 alkyl benzoates, hexyl laurate, diisopropyl adipate, isononyl isononanoate, 2-ethylhexyl palmitate, isostearyl isostearate, 2-hexyldecyl laurate, 2-octyldecyl palmitate, 2-octyldodecyl myristate, alkyl or polyalkyl heptanoates, octanoates, decanoates or ricinoleates such as propylene glycol dioctanoate; hydroxylated esters such as isostearyl lactate, diisostearyl malate and 2-octyldodecyl lactate; polyol esters and pentaerythritol esters, fatty alcohols that are liquid at room temperature, with a branched and/or unsaturated carbon-based chain containing from 12 to 26 carbon atoms, for instance octyldodecanol, isostearyl alcohol, oleyl alcohol, 2-hexyldecanol, 2-butyloctanol and 2-undecylpentadecanol.

Preferably, the hydrocarbon-based oil is apolar (formed solely from carbon and hydrogen atoms).

The hydrocarbon-based oil is preferably chosen from hydrocarbon-based oils containing from 8 to 14 carbon atoms, in particular the apolar oils described previously. Preferably, the hydrocarbon-based oil is isododecane.

The polymer particles of the dispersion preferably have an average size, especially a number-average size, ranging from about 50 to about 500 nm, preferably ranging from about 75 to about 400 nm, and preferably ranging from about 100 to about 250 nm, including all ranges and subranges therebetween.

In general, the dispersion according to the invention may be prepared in the following manner, which is given as an example.

The polymerization may be performed in dispersion, i.e. by precipitation of the polymer during formation, with protection of the formed particles with a stabilizer. In a first step, the stabilizing polymer is prepared by mixing the constituent monomer(s) of the stabilizing polymer, with a radical initiator, in a solvent known as the synthesis solvent, and by polymerizing these monomers. In a second step, the constituent monomer(s) of the polymer of the particles are added to the stabilizing polymer formed and polymerization of these added monomers is performed in the presence of the radical initiator.

When the non-aqueous medium is a non-volatile hydrocarbon-based oil, the polymerization may be performed in an apolar organic solvent (synthesis solvent), followed by adding the non-volatile hydrocarbon-based oil (which should be miscible with the said synthesis solvent) and selectively distilling off the synthesis solvent. A synthesis solvent which is such that the monomers of the stabilizing polymer and the free-radical initiator are soluble therein, and the polymer particles obtained are insoluble therein, so that they precipitate therein during their formation, is thus chosen. In particular, the synthesis solvent may be chosen from alkanes such as heptane or cyclohexane.

When the non-aqueous medium is a volatile hydrocarbon-based oil, the polymerization may be performed directly in the oil, which thus also acts as synthesis solvent. The monomers should also be soluble therein, as should the free-radical initiator, and the polymer of the particles obtained should be insoluble therein.

The monomers are preferably present in the synthesis solvent, before polymerization, in a proportion of about 5 to about 20% by weight. The total amount of monomers may be present in the solvent before the start of the reaction, or part of the monomers may be added gradually as the polymerization reaction proceeds. The free-radical initiator is preferably azobisisobutyronitrile or tert-butyl peroxy-2-ethylhexanoate.

The polymerization may be performed at a temperature ranging from about 70 to about 110° C.

The polymer particles are surface-stabilized, when they are formed during the polymerization, by means of the stabilizer.

The stabilization may be performed by any known means, and in particular by direct addition of the stabilizer, during the polymerization. The stabilizer is preferably also present in the mixture before polymerization of the monomers of the polymer of the particles. However, it is also possible to add it continuously, especially when the monomers of the polymer of the particles are also added continuously.

From about 10% to about 30% by weight, preferably from about 15% to about 25% by weight of stabilizer may be used, relative to the total weight of monomers used (stabilizer+polymer of the particles).

The polymer particle dispersion preferably comprises from about 30% to about 65% by weight, preferably from about 40% to about 60% by weight of solids, relative to the total weight of the dispersion.

Preferably, the oily dispersion may comprise a plasticizer, for example, a plasticizer chosen from tri-n-butyl citrate, tripropylene glycol monomethyl ether (INCI name: PPG-3 methyl ether) and trimethyl pentaphenyl trisiloxane (sold under the name Dow Corning PH-1555 HRI Cosmetic Fluid by the company Dow Corning). These plasticizers make it possible to improve the mechanical strength of the polymer film. The plasticizer, if present, may be present in the oily dispersion in an amount ranging from about 5% to about 50% by weight, relative to the total weight of the polymer of the particles.

According to preferred embodiments, the polymer of the particles is a C1-C4 alkyl (meth)acrylate polymer; the stabilizer is an isobornyl(meth)acrylate polymer chosen from isobornyl(meth)acrylate homopolymer and statistical copolymers of isobornyl(meth)acrylate and of C1-C4 alkyl (meth)acrylate present in an isobornyl(meth)acrylate/C1-C4 alkyl(meth)acrylate weight ratio of greater than 4. For these statistical stabilizing copolymers, the defined weight ratio makes it possible to obtain a polymer dispersion that is stable, especially after storage for seven days at room temperature (25° C.).

The dispersions according to the invention consist of particles, which are generally spherical, of at least one surface-stabilized polymer, in a non-aqueous medium.

Preferably, the amount of acrylic polymer particles present in the compositions of the present invention ranges from about 5 to about 60% by weight based on total weight of the composition, preferably about 7% to about 40% by weight based on the total weight of the composition, preferably about 10% to about 25% by weight based on the total weight of the composition, including all ranges and subranges therebetween.

Plasticizer

According to the present invention, compositions containing at least about 15% by weight with respect to the weight of the composition of at least one plasticizing agent are provided. According to preferred embodiments, the plasticizer(s) are selected from the group consisting of plasticizers containing at least one ester group, plasticizers containing at least one phenyl group, and mixtures thereof. The ester group as well as the phenyl group in both types of plasticizers may be substituted or unsubstituted.

Suitable examples of plasticizers containing at least one ester group are plasticizing agents which are esters of carboxylic acids such as, for example, citrates such as triethyl citrate, tributyl citrate, triethyl acetylcitrate, tributyl acetylcitrate, and 2-triethylhexyl acetylcitrate; benzoates such as benzyl benzoate; glycolates such as butyl glycolate; tartrates such as dibutyl tartrate; and acetates such as glyceryl triacetate, and mixtures thereof. Preferably, the plasticizing agent containing at least one ester group is an ester of a citrate. Preferably, the plasticizing agent containing at least one ester group is tributyl citrate.

Suitable examples of plasticizing agents containing at least one phenyl group are plasticizing agents which are phenylated silicones, particularly phenylated trimethicones, such as phenyl trimethicone and pentaphenyl trimethicone. Alternatively, suitable examples of plasticizing agents containing at least one phenyl group are plasticizing agents which are phenylated hydrocarbons such as benzyl benzoate.

According to preferred embodiments, compositions of the present invention contain at least two plasticizing agents, and the total amount of plasticizing agents present is at least about 15% by weight with respect to the weight of the composition.

According to preferred embodiments, the total amount of plasticizers present in the compositions of the present invention is greater than about 15% by weight, preferably greater than about 17% by weight, and preferably greater than about 19% by weight with respect to the weight of the composition, including ranges such as between about 15% and about 50% by weight, preferably between about 17% and about 40% by weight, and preferably between about 19% and about 30% by weight of the weight of the composition, including all ranges and subranges therebetween.

In embodiments where at least two plasticizing agents are present in the compositions of the present invention, it is preferred that at least one plasticizer containing at least one ester group and at least one plasticizer containing at least one phenyl group are present in the composition, and that (1) the weight ratio of plasticizer(s) containing at least one ester group and at least one plasticizer(s) containing at least one phenyl group is preferably from 2.5:1 to 1:2.5, preferably 2.4:1 to 1:2.4 and (2) the weight ratio of acrylic polymer particles particles to plasticizer(s) is preferably from 2:1 to 1:1, preferably 2:1 to 1.2:1.

Volatile Oil

According to the present invention, compositions containing at least one volatile oil are provided. Any suitable volatile oil can be used. The volatile oil may be present as part of or in association with the at least one dispersion of acrylic polymer particles. The volatility of oils can be determined using any means known in the art such as, for example, the evaporation speed as set forth in U.S. Pat. No. 6,338,839, hereby incorporated by reference.

According to preferred embodiments, the at least one volatile oil is a non-silicone volatile oil. Suitable volatile non-silicone oils include but are not limited to volatile hydrocarbon oils, volatile alcohols, volatile esters and volatile ethers. Examples of such volatile non-silicone oils include, but are not limited to, volatile hydrocarbon oils having from 8 to 16 carbon atoms and their mixtures and in particular branched $C_8$ to $C_{16}$ alkanes such as $C_8$ to $C_{16}$ isoalkanes (also known as isoparaffins), isododecane, isodecane, isohexadecane, and for example, the oils sold under the trade names of Isopar or Permethyl, the $C_8$ to $C_{16}$ branched esters such as isohexyl or isodecyl neopentanoate and their mixtures. Preferably, the volatile non-silicone oils have a flash point of at least 40° C.

Non-limiting examples of volatile non-silicone volatile oils are given in Table 1 below.

TABLE 1

| Compound | Flash Point (° C.) |
| --- | --- |
| Isododecane | 43 |
| Isohexadecane | 101 |
| Propylene glycol n-butyl ether | 60 |
| Ethyl 3-ethoxypropionate | 58 |
| Propylene glycol methylether acetate | 46 |
| Isopar L (isoparaffin C11-C13) | 62 |
| Isopar H (isoparaffin C11-C12) | 56 |

According to preferred embodiments, the at least one volatile oil is a silicone volatile oil. According to particularly preferred embodiments, the volatile silicone oil is a cyclic volatile silicone oil.

Suitable volatile silicone oils include but are not limited to linear or cyclic silicone oils having a viscosity at room temperature less than or equal to 6 cSt and having from 2 to 7 silicon atoms, these silicones being optionally substituted with alkyl or alkoxy groups of 1 to 10 carbon atoms. Specific oils that may be used in the invention include octamethyltetrasiloxane, decamethylcyclopentasiloxane, dodecamethylcyclohexasiloxane, heptamethyloctyltrisiloxane, hexamethyldisiloxane, decamethyltetrasiloxane, dodecamethylpentasiloxane and their mixtures. Other volatile oils which may be used include KF 96A of 6 cSt viscosity, a commercial product from Shin Etsu having a flash point of 94° C. Preferably, the volatile silicone oils have a flash point of at least 40° C.

Non-limiting examples of volatile silicone oils are listed in Table 2 below.

TABLE 2

| Compound | Flash Point (° C.) | Viscosity (cSt) |
| --- | --- | --- |
| Octyltrimethicone | 93 | 1.2 |
| Hexyltrimethicone | 79 | 1.2 |
| Decamethylcyclopentasiloxane (cyclopentasiloxane or D5) | 72 | 4.2 |
| Octamethylcyclotetrasiloxane (cyclotetradimethylsiloxane or D4) | 55 | 2.5 |
| Dodecamethylcyclohexasiloxane (D6) | 93 | 7 |
| Decamethyltetrasiloxane(L4) | 63 | 1.7 |
| KF-96 A from Shin Etsu | 94 | 6 |
| PDMS (polydimethylsiloxane) DC 200 (1.5 cSt) from Dow Corning | 56 | 1.5 |
| PDMS DC 200 (2 cSt) from Dow Corning | 87 | 2 |

According to preferred embodiments, the volatile oil(s) is/are preferably present in an amount of about 5 to 80 percent by weight, preferably from about 15 to about 60 percent by weight, preferably from 20 to about 55 percent by weight, and preferably from about 25 to about 54 percent by weight of the total weight of the composition, including all ranges and subranges therebetween.

Coloring Agent

According to the present invention, compositions comprising at least one coloring agent are provided. In the compositions of the present invention, any coloring agent can be used. The at least one coloring agent is preferably chosen from pigments, dyes such as liposoluble dyes, nacreous pigments, and/or pearling agents.

Representative liposoluble dyes which may be used according to the present invention include Sudan Red, DC Red 17, DC Green 6, β-carotene, soybean oil, Sudan Brown, DC Yellow 11, DC Violet 2, DC Orange 5, annatto, and quinoline yellow. The liposoluble dyes, when present, generally have a concentration ranging up to 20% by weight of the total weight of the composition, preferably from 0.0001% to 6%, including all ranges and subranges therebetween.

The nacreous pigments which may be used according to the present invention include but are not limited to nacreous pigments such as mica coated with titanium or with bismuth oxychloride, colored nacreous pigments such as titanium mica with iron oxides, titanium mica with ferric blue or chromium oxide, titanium mica with an organic pigment chosen from those mentioned above, and nacreous pigments based on bismuth oxychloride. The nacreous pigments, if present, may be present in the composition in a concentration ranging up to 50% by weight of the total weight of the composition, preferably from 0.1% to 20%, and preferably from 0.1% to 15%, including all ranges and subranges therebetween.

The pigments, which may be used according to the present invention, may be chosen from white, colored, inorganic, organic, polymeric, nonpolymeric, coated and uncoated pigments. Representative examples of mineral pigments include titanium dioxide, optionally surface-treated, zirconium oxide, zinc oxide, cerium oxide, iron oxides, chromium oxides, manganese violet, ultramarine blue, chromium hydrate, and ferric blue. Representative examples of organic pigments include carbon black, pigments of D & C type, and lakes based on cochineal carmine, barium, strontium, calcium, and aluminum. The pigments are preferably present in the composition in a concentration ranging up to 50% by weight of the total weight of the composition, preferably from 1% to 30%, and preferably from 1% to 15%, including all ranges and subranges therebetween.

Thickening Agent

According to the present invention, compositions comprising at least one thickening agent are provided. Preferably, the at least one thickening agent is/are selected from the group consisting of polar thickening agents, apolar thickening agents, and mixtures thereof.

According to preferred embodiments, compositions comprising at least one polar thickening agent are provided. Preferably, the at least one polar thickening agent is a wax. "Wax" as used herein means a lipophilic compound that is solid at room temperature (25° C.), with a solid/liquid reversible change of state, having a melting point of greater than or equal to 30° C., which may be up to 200° C., and in particular up to 120° C., including all ranges and subranges therebetween. Preferred waxes are those having a melting point of greater than or equal to 45° C. and in particular greater than or equal to 55° C.

"Polar wax" as used herein means a wax whose solubility parameter at 25° C., $\delta_a$, is other than 0 $(J/cm^3)^{1/2}$. "Polar wax" refers to a wax whose chemical structure is formed essentially from, or even constituted by, carbon and hydrogen atoms, and comprising at least one highly electronegative heteroatom such as an oxygen, nitrogen or phosphorus atom. The definition and calculation of the solubility parameters in the Hansen three-dimensional solubility space are described in the article by C. M. Hansen: "The three dimensional solubility parameters" J. Paint Technol. 39, 105 (1967). According to this Hansen space:

$\delta_D$ characterizes the London dispersion forces derived from the formation of dipoles induced during molecular impacts;

$\delta_p$ characterizes the Debye interaction forces between permanent dipoles and also the Keesom interaction forces between induced dipoles and permanent dipoles;

$\delta_h$ characterizes the specific interaction forces (such as hydrogen bonding, acid/base, donor/acceptor, etc.); and $\delta_a$ is determined by the equation: $\delta_a = (\delta_p^2 + \delta_h^2)^{1/2}$.

The parameters $\delta_p$, $\delta_h$, $\delta_D$ and $\delta_a$ are expressed in $(J/cm^3)^{1/2}$.

The waxes that may be used in the compositions according to the invention are chosen from waxes that are solid at room temperature of animal, plant, mineral and/or synthetic origin, and mixtures thereof. Preferably, the waxes are hydrocarbon-based or silicone waxes "Hydrocarbon-based wax" means a wax formed essentially from, or even constituted by, carbon and hydrogen atoms, and possibly oxygen and nitrogen atoms, and not containing any silicon or fluorine atoms. It may contain groups such as, for example, alcohol, ester, ether, carboxylic acid, amine and/or amide groups. "Silicone wax" means compounds comprising at least one silicon atom, preferably comprising Si—O groups.

Preferably, the polar wax is hydrocarbon-based. Suitable hydrocarbon-based waxes include, for example, beeswax, lanolin wax, rice bran wax, carnauba wax, candelilla wax, shellac wax; montan wax, orange wax and lemon wax, laurel wax and olive wax. Ester waxes (waxes comprising at least one ester function or group) are also preferred. Suitable examples of ester waxes include, for example, $C_{20}$-$C_{40}$ alkyl(hydroxystearyloxy)stearate (the alkyl group containing from 20 to 40 carbon atoms), alone or as a mixture, or a $C_{20}$-$C_{40}$-alkyl stearate. Specific examples of such waxes are sold under the names Kester Wax K 82 P®, Hydroxypolyester K 82 P®, Kester Wax K 80 P®. or Kester Wax K82H by the company Koster Keunen. Other specific examples include esters of polyethylene glycol and of montanic acid (octacosanoic acid), such as the wax Licowax KPS Flakes (INCI name: glycol montanate) sold by the company Clariant. Alcohol waxes (waxes comprising at least one alcohol function, i.e. comprising at least one free hydroxyl (OH) group) are also preferred. Suitable examples of alcohol waxes include but are not limited to alcohol waxes commercially available from Baker Hughes under the Performacol trade name such as, for example, Performacol 350 (INCI Name: C20-C40 alcohols), 425 (INCI Name: C20-C40 alcohols) and 550 (INCI Name: C30-C50 alcohols). Another example of a commercial product comprising a suitable alcohol wax is Performacol 550-L Alcohol from New Phase Technologies.

According to preferred embodiments, the at least one thickening agent is a polar paste (polar pasty compound). "Paste" or "pasty compound" means a lipophilic fatty compound that undergoes a reversible solid/liquid change of state and that comprises in the solid state an anisotropic crystal organization, and comprises, at a temperature of 23° C., a liquid fraction and a solid fraction. In other words, the starting melting point of the pasty compound is less than 23° C. The liquid fraction of the pasty compound measured at 23° C. preferably represents 9% to 97% by weight of the compound. This liquid fraction at 23° C., preferably between 15% and 85% and preferably between 40% and 85% by weight, including all ranges and subranges therebetween.

The liquid fraction by weight of the pasty compound at 23° C. is about equal to the ratio of the heat of fusion consumed at 23° C. to the heat of fusion of the pasty compound. The heat of fusion of the pasty compound is the heat consumed by the compound to change from the solid state to the liquid state. The pasty compound is said to be in the solid state when all of its mass is in solid form. The pasty compound is said to be in the liquid state when all of its mass is in liquid form. The heat of fusion of the pasty compound is about equal to the area under the curve of the thermogram obtained using a differential scanning calorimeter (DSC), such as the calorimeter sold under the name MDSC 2920 by the company TA Instrument, with a temperature rise of 5 or 10° C. per minute, according to standard ISO 11357-3:1999. The heat of fusion of the pasty compound is the amount of energy required to make the compound change from the solid state to the liquid state. It is expressed in J/g.

The heat of fusion consumed at 23° C. is the amount of energy absorbed by the sample to change from the solid state to the state that it has at 23° C., constituted of a liquid fraction and a solid fraction.

The liquid fraction of the pasty compound, measured at 32° C., preferably represents from 30% to 100% by weight of the compound, preferably from 50% to 100% and preferably from 60% to 100% by weight of the compound, including all ranges and subranges therebetween. When the liquid fraction of the pasty compound measured at 32° C. is equal to 100%, the temperature of the end of the melting range of the pasty compound is less than or equal to 32° C.

The liquid fraction of the pasty compound measured at 32° C. is about equal to the ratio of the heat of fusion consumed at 32° C. to the heat of fusion of the pasty compound. The heat of fusion consumed at 32° C. is calculated in the same manner as the heat of fusion consumed at 23° C.

The pasty compound is preferably chosen from synthetic compounds and compounds of plant origin. A pasty compound may be obtained by synthesis from starting materials of plant origin. Preferably, the pasty compound is chosen from polyethers and esters. Preferred polyethers are liposoluble polyethers resulting from the polyetherification between one or more $C_2$-$C_{100}$ and preferably $C_2$-$C_{50}$ diols. Preferred esters include, for example, glycerol oligomer, especially diglycerol esters, in particular condensates of adipic acid and of glycerol, for which some of the hydroxyl groups of the glycerols have reacted with a mixture of fatty acids such as stearic acid, capric acid, stearic acid and isostearic acid, and 12-hydroxystearic acid, especially such as the product sold under the brand name Softisan 649 by the company Sasol.

According to preferred embodiments, the at least one thickening agent is an apolar wax. For the purposes of the present invention, the term "apolar wax" means a wax whose solubility parameter at 25° C. as defined herein ($\delta_a$, is equal to 0 $(J/cm^3)^{1/2}$. Apolar waxes are in particular hydrocarbon-based waxes formed solely from carbon and hydrogen atoms, and free of heteroatoms such as N, O and P. In particular, the term "apolar wax" means a wax that is formed exclusively from apolar wax and not from a mixture also comprising other types of waxes that are not apolar waxes.

Suitable examples of apolar waxes include hydrocarbon-based waxes, for instance microcrystalline waxes, paraffin waxes, ozokerite and polyethylene waxes. Polyethylene waxes that may be mentioned include Performalene 500-L Polyethylene and Performalene 400 Polyethylene sold by New Phase Technologies. An ozokerite that may be mentioned is Ozokerite Wax SP 1020 P. Examples of microcrystalline waxes include Multiwax W 445® sold by the company Sonneborn and Microwax HW® and Base Wax 30540® sold by the company Paramelt. Examples of microwaxes that may be used in the compositions according to the invention as apolar waxes include polyethylene microwaxes such as those sold under the names Micropoly 200®, 220®, 220L®, and 250S® by the company Micro Powders.

According to preferred embodiments in which the compositions of the present invention are not solid, suitable thickening agents can be gelling agents. Preferred gelling agents are modified clays. Non-limiting examples of such gelling agents include hectorite modified with distearyldimethylammonium chloride or modified with stearyldimethylbenzoylammonium chloride. A preferred gelling agent is disteardimonium hectorite, which is commercially available, for example, from Elementis under the tradename Bentone Gel (disteardimonium hectorite (and) propylene carbonate).

Other useful gelling agents include silica, such as fumed silica. The fumed silica may have a particle size, which may be nanometric to micrometric, for example ranging from about 5 nm to 200 nm. Particularly useful fumed silicas are those that are finely divided, hydrophilic and having a large number of silanol groups at their surface. Such hydrophilic silicas are available, for example, under the following tradenames, all of which have the INCI name of silica: "Aerosil 130®", "Aerosil 200®", "Aerosil 255®", "Aerosil 300®" and "Aerosil 380®", from the company Degussa, and "CAB-O-SIL HS-5®", "CAB-O-SIL EH-5®", "CAB-O-SIL LM-130®", "CAB-O-SIL MS-55®" and "CAB-O-SIL M-5®" from Cabot."

According to preferred embodiments, the thickening agent(s) is preferably present in the composition in an amount ranging from about 1% to about 40% by weight relative to the total weight of the composition. Preferably, the thickening agent(s) is present in an amount ranging from about 2% to about 35% by weight relative to the total weight of the composition, and more preferably from about 5% to about 30%.

Optional Ingredients

The compositions of the invention can also optionally comprise any additive usually used in such compositions. For example, oils, organogelators, dispersants, antioxidants, vitamins, emollients, preserving agents, fragrances, fillers, neutralizing agents, cosmetic and dermatological active agents, moisturizers, humectants, water, sunscreen agents, gelling agents, elastomers, short chain esters, surfactants, and mixtures thereof can be added, if desired. Further examples of suitable optional components can be found in the references which have been incorporated by reference in this application. Still further examples of such additional ingredients may be found in the International Cosmetic Ingredient Dictionary and Handbook ($9^{th}$ ed. 2002).

A person of ordinary skill in the art will take care to select the optional additional additives and/or the amount thereof such that the advantageous properties of the compositions, kits and methods according to the invention are not, or are not substantially, adversely affected by the envisaged addition.

Such additives may be present in the composition in a proportion from 0% to 90% relative to the total weight of the composition, preferably from 0.01% to 85%, and most preferably from 10 to 80% (if present).

The compositions according to the invention are preferably intended for topical application to keratinous material such as the skin and/or lips. Accordingly, the compositions of the present invention preferably contain a physiologically acceptable medium. Of course, the components of the physiologically acceptable medium of the present invention will depend upon the intended use of the composition as one of ordinary skill in the art would understand that different cosmetic compositions generally contain ingredients useful for the specific type of composition. Needless to say, the composition of the invention should be cosmetically or dermatologically acceptable, i.e., it should contain a non-toxic physiologically acceptable medium and should be able to be applied to the skin, superficial body growths or the lips of human beings.

According to preferred embodiments of the present invention, methods of treating, caring for and/or making up keratinous material such as skin or lips by applying compositions of the present invention to the keratinous material in an amount sufficient to treat, care for and/or make up the keratinous material are provided.

According to other preferred embodiments, methods of covering or hiding defects associated with keratinous material such as imperfections or discolorations by applying compositions of the present invention to the keratinous material in an amount sufficient to cover or hide such defects are provided.

According to yet other preferred embodiments, methods of enhancing the appearance of keratinous material by applying compositions of the present invention to the keratinous material in an amount sufficient to enhance the appearance of the keratinous material are provided.

In accordance with the three preceding preferred embodiments, the compositions of the present invention are applied topically to the desired area of the keratinous material (e.g., skin or lips) in an amount sufficient to treat, care for and/or make up the keratinous material, to cover or hide defects associated with keratinous material, skin imperfections or discolorations, or to enhance the appearance of keratinous material. The compositions may be applied to the desired area as needed, preferably once or twice daily, more preferably once daily and then preferably allowed to dry before subjecting to contact such as with clothing or other objects. The composition is preferably applied to the desired area that is dry or has been dried prior to application.

According to preferred embodiments of the present invention, compositions having improved cosmetic properties such as, for example, improved long wear, transfer resistance or waterproof properties are provided. The improved properties may also be chosen from improved flexibility, wearability, drying time or retention as well as reduced tackiness or migration over time.

In accordance with yet another embodiment of the present invention, kits comprising a composition comprising at least one dispersion of acrylic polymer particles, at least one volatile oil, at least one coloring agent, at least one thickening agent, and at least about 15% by weight with respect to the weight of the composition of at least one plasticizing agent are provided. In addition to this composition, the kits of the present invention can further comprise one or more compositions such as, for example, compositions to be applied on top of make-up compositions (for example, glosses or topcoats), compositions to be applied underneath make-up compositions (for example, primers or basecoats), and compositions for removing make-up from keratin materials. Any suitable topcoat, basecoat or removal composition can be included in such kits.

The packaging and application device for any such kit or compositions in the kit may be chosen and manufactured by persons skilled in the art on the basis of their general knowledge, and adapted according to the nature of the compositions to be packaged. Indeed, the type of device to be used can be in particular linked to the consistency of the composition, in particular to its viscosity; it can also depend on the nature of the constituents present in the compositions.

According to yet other preferred embodiments, methods of making a composition comprising combining at least one dispersion of acrylic polymer particles, at least one volatile oil, at least one coloring agent, at least one thickening agent, and at least about 15% by weight with respect to the weight of the composition of at least one plasticizing agent during preparation are provided.

Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention.

Notwithstanding that the numerical ranges and parameters setting forth the broad scope of the invention are approximations, the numerical values set forth in the specific examples are reported as precisely as possible. Any numerical value, however, inherently contain certain errors necessarily resulting from the standard deviation found in their respective measurements. The following examples are intended to illustrate the invention without limiting the scope as a result. The percentages are given on a weight basis.

Preparation of Dispersion of Acrylic Polymer Particles

Example 1

In a first step, 1300 g of isododecane, 337 g of isobornyl acrylate, 28 g of methyl acrylate and 3.64 g of tert-butyl peroxy-2-ethylhexanoate (Trigonox 21S from Akzo) were placed in a reactor. The isobornyl acrylate/methyl acrylate mass ratio is 92/8. The mixture was heated at 90° C. under argon with stirring.

After 2 hours of reaction, 1430 g of isododecane were added to the reactor feedstock and the mixture was heated to 90° C.

In a second step, a mixture of 1376 g of methyl acrylate, 1376 g of isododecane and 13.75 g of Trigonox 21S were run in over 2 hours 30 minutes, and the mixture was left to react for 7 hours. 3.3 liters of isododecane were then added and part of the isododecane was evaporated off to obtain a solids content of 50% by weight.

A dispersion of methyl acrylate particles stabilized with a statistical copolymer stabilizer containing 92% isobornyl acrylate and 8% methyl acrylate in isododecane was obtained.

The oily dispersion contains in total (stabilizer+particles) 80% methyl acrylate and 20% isobornyl acrylate.

The polymer particles of the dispersion have a number-average size of about 160 nm.

The dispersion is stable after storage for 7 days at room temperature (25° C.).

Example 2

A dispersion of polymer in isododecane was prepared according to the preparation method of Example 1, using:

Step 1: 275.5 g of isobornyl acrylate, 11.6 g of methyl acrylate, 11.6 g of ethyl acrylate, 2.99 g of Trigonox 21, 750 g of isododecane; followed by addition, after reaction, of 750 g of isododecane.

Step 2: 539.5 g of methyl acrylate, 539.5 g of ethyl acrylate, 10.8 g of Trigonox 21S, 1079 g of isododecane. After reaction, addition of 2 liters of isododecane and evaporation to obtain a solids content of 35% by weight.

A dispersion in isododecane of methyl acrylate/ethyl acrylate (50/50) copolymer particles stabilized with an isobornyl acrylate/methyl acrylate/ethyl acrylate (92/4/4) statistical copolymer stabilizer was obtained.

The oily dispersion contains in total (stabilizer+particles) 40% methyl acrylate, 40% ethyl acrylate and 20% isobornyl acrylate.

The dispersion is stable after storage for 7 days at room temperature (25° C.).

Example 3

A dispersion of polymer in isododecane was prepared according to the preparation method of Example 1, using:

Step 1: 315.2 g of isobornyl acrylate, 12.5 g of methyl acrylate, 12.5 g of ethyl acrylate, 3.4 g of Trigonox 21, 540 g of isododecane, 360 g of ethyl acetate; followed by addition, after reaction, of 540 g of isododecane and 360 g of ethyl acetate.

Step 2: 303 g of methyl acrylate, 776 g of ethyl acrylate, 157 g of acrylic acid, 11 g of Trigonox 21S, 741.6 g of isododecane and 494.4 g of ethyl acetate. After reaction, addition of 3 liters of an isododecane/ethyl acetate mixture (60/40 weight/weight) and total evaporation of the ethyl acetate and partial evaporation of the isododecane to obtain a solids content of 44% by weight.

A dispersion in isododecane of methyl acrylate/ethyl acrylate/acrylic acid (24.5/62.8/12.7) copolymer particles stabilized with an isobornyl acrylate/methyl acrylate/ethyl acrylate (92/4/4) statistical copolymer stabilizer was obtained.

The oily dispersion contains in total (stabilizer+particles) 10% acrylic acid, 20% methyl acrylate, 50% ethyl acrylate and 20% isobornyl acrylate.

The dispersion is stable after storage for 7 days at room temperature (25° C.).

Example 4

A dispersion of polymer in isododecane was prepared according to the preparation method of Example 1, using:

Step 1: 315.2 g of isobornyl acrylate, 12.5 g of methyl acrylate, 12.5 g of ethyl acrylate, 3.4 g of Trigonox 21, 540 g of isododecane, 360 g of ethyl acetate; followed by addition, after reaction, of 540 g of isododecane and 360 g of ethyl acetate.

Step 2: 145 g of methyl acrylate, 934 g of ethyl acrylate, 157 g of acrylic acid, 12.36 g of Trigonox 21S, 741.6 g of isododecane and 494.4 g of ethyl acetate. After reaction, addition of 3 liters of an isododecane/ethyl acetate mixture (60/40 weight/weight) and total evaporation of the ethyl acetate and partial evaporation of the isododecane to obtain a solids content of 44% by weight.

A dispersion in isododecane of methyl acrylate/ethyl acrylate/acrylic acid (11.7/75.6/12.7) copolymer particles stabilized with an isobornyl acrylate/methyl acrylate/ethyl acrylate (92/4/4) statistical copolymer stabilizer was obtained.

The oily dispersion contains in total (stabilizer+particles) 10% acrylic acid, 10% methyl acrylate, 60% ethyl acrylate and 20% isobornyl acrylate.

The dispersion is stable after storage for 7 days at room temperature (25° C.).

Example 5

A dispersion of polymer in isododecane was prepared according to the preparation method of Example 1, using:

Step 1: 48 g of isobornyl acrylate, 2 g of methyl acrylate, 2 g of ethyl acrylate, 0.52 g of Trigonox 21, 57.6 g of isododecane, 38.4 g of ethyl acetate; followed by addition, after reaction, of 540 g of isododecane and 360 g of ethyl acetate.

Step 2: 98 g of methyl acrylate, 73 g of ethyl acrylate, 25 g of maleic anhydride, 1.96 g of Trigonox 21S, 50.4 g of isododecane and 33.60 g of ethyl acetate. After reaction, addition of 1 liter of an isododecane/ethyl acetate mixture (60/40 weight/weight) and total evaporation of the ethyl acetate and partial evaporation of the isododecane to obtain a solids content of 46.2% by weight.

A dispersion in isododecane of methyl acrylate/ethyl acrylate/maleic anhydride (50/37.2/12.8) copolymer particles stabilized with an isobornyl acrylate/methyl acrylate/ethyl acrylate (92/4/4) statistical copolymer stabilizer was obtained.

The oily dispersion contains in total (stabilizer+particles) 10% maleic anhydride, 30% methyl acrylate, 40% ethyl acrylate and 20% isobornyl acrylate.

The dispersion is stable after storage for 7 days at room temperature (25° C.).

Example 6

A dispersion of polymer in isododecane was prepared according to the preparation method of Example 1, using:

Step 1: 48.5 g of isobornyl methacrylate, 4 g of methyl acrylate, 0.52 g Trigonox 21, 115 g of isododecane; followed by addition, after reaction, of 80 g of isododecane.

Step 2: 190 g of methyl acrylate, 1.9 g of Trigonox 21S, 190 g of isododecane. After reaction, addition of 1 liter of isododecane and partial evaporation of the isododecane to obtain a solids content of 48% by weight.

A dispersion in isododecane of methyl acrylate polymer particles stabilized with an isobornyl methacrylate/methyl acrylate (92/8) statistical copolymer stabilizer was obtained.

The oily dispersion contains in total (stabilizer+particles) 80% methyl acrylate and 20% isobornyl methacrylate.

The dispersion is stable after storage for 7 days at room temperature (25° C.).

Examples 7 and 8

Several oily dispersions of polymethyl acrylate stabilized with a stabilizer containing isobornyl acrylate and optionally methyl acrylate were prepared, according to the procedure of Example 1, by varying the mass ratio of isobornyl acrylate and methyl acrylate and observing the stability of the dispersion obtained as a function of the chemical constitution of the stabilizer.

All the dispersions comprise in total (stabilizer+particles) 80% methyl acrylate and 20% isobornyl acrylate.

Example 7

Step 1: 50 g of isobornyl acrylate, 0.5 g Trigonox 21, 96 g of isododecane; followed by addition, after reaction, of 80 g of isododecane.

Step 2: 200 g of methyl acrylate, 2 g of Trigonox 21S, 200 g of isododecane. After reaction, addition of 80 g of isododecane and evaporation to obtain a solids content of 31% by weight.

A dispersion in isododecane of polymethyl acrylate particles stabilized with a polyisobornyl acrylate stabilizer was obtained.

Example 8

Step 1: 48.5 g of isobornyl acrylate, 8.5 g of methyl acrylate, 0.57 g Trigonox 21, 115 g of isododecane; followed by addition, after reaction, of 75 g of isododecane.

Step 2: 185.5 g of methyl acrylate, 1.85 g of Trigonox 21S, 185.5 g of isododecane. After reaction, addition of 75 g of isododecane and evaporation to obtain a solids content of 31% by weight.

A dispersion in isododecane of polymethyl acrylate particles stabilized with an isobornyl acrylate/methyl acrylate (85/15) statistical copolymer stabilizer was obtained.

Flake Protocol:

On a slab of bioskin within a 2×3 cm area, lipstick was applied by hand using 10 strokes. The sample was allowed to dry for twenty minutes. Following the drying step, the sample was stretched in two directions twice respectively. The film quality in terms of flaking was ranked on a scale of 1-3, in which 1 is no flaking, 2 are intermediate, and 3 is complete flaking.

Oil Resistance Protocol:

On a slab of bioskin within a 2×3 cm area, lipstick was applied by hand using 10 strokes. The sample was allowed to dry for twenty minutes. Following the drying step, an olive oil droplet was placed on top of the lipstick film and allowed to soak for ten minutes. Following the soaking step, the oil was wiped off 5 times using a kimwipe. The film quality in terms of oil resistance was ranked on a scale of 1-3, in which 1 is excellent resistance, 2 is intermediate, and 3 is bad resistance to removal.

Example 9

Single Plasticizer

TABLE 3

| Ingredient Name | Comparative Example 9A | Comparative Example 9B | Invention Example 9C | Comparative Example 9D | Invention Example 9E |
|---|---|---|---|---|---|
| Oil Dispersion Example 3 | 51.02 | 51.02 | 51.02 | 51.02 | 51.02 |
| Tributyl citrate | 0 | 5 | 19.43 | 0 | 0 |
| Trimethyl pentaphenyl dimethicone | 0 | 0 | 0 | 10 | 19.43 |
| Isohexadecane | 8 | 8 | 8 | 8 | 8 |
| Alcohol Wax | 1 | 1 | 1.25 | 1.25 | 1.25 |
| Polyethylene Wax | 13 | 13 | 13 | 13 | 13 |
| Mica | 3 | 3 | 3 | 3 | 3 |
| Red 7 | 4.3 | 4.3 | 4.3 | 4.3 | 4.3 |
| Isododecane | 19.68 | 14.68 | 0 | 9.43 | 0 |
| Oil Dispersion Solid:Plasticizer | 1:0 | 5:1 | 1.29:1 | 2.5:1 | 1.29:1 |
| Flake | 3 | 3 | 1 | 2 | 1 |
| Oil Resistance | 3 | 1 | 1 | 2 | 1 |

Preparation of Lip Compositions

The following invention and comparative examples were prepared and evaluated according to the protocols described below. The results of the evaluation are provided in the table.

Lipstick

Waxes, and a portion of isododecane were blended under high shear at 110° C. until all materials were completely blended. Pigments, oil dispersions, and plasticizers were blended separately in a portion of isododecane. The solution temperature was brought down to 65° C. of the first mixture and the pigment solution, mica and the final amount of isododecane was added to the mixture and blended until homogenous. Sticks were poured in a slim lipstick mold and allowed to reach room temperature over the course of 30 minutes. The mold was then chilled on a cooling plate for an addition 20 minutes. Sticks were individually transferred into standard lipstick components and allowed to equilibrate at room temperature for 24 hours.

Also, commercial products were evaluated according to the same protocols. Commercial comparative example A contained MQ resin. Commercial comparative example B contains polypropylsilsesquioxane. The results of the evaluation are set forth below.

TABLE 4

| Test | Commercial Comparative Example A MQ/Dimethicone | Commercial Comparative Example B Polypropylsilsesquioxane |
|---|---|---|
| Flake | 1 | 1 |
| Oil Resistance | 3 | 3 |

As shown above, oil dispersion samples without the presence of plasticizer yielded a lipstick with poor wear properties in terms of resistance to flaking and oil resistance by in-vitro testing. Incorporation of tributyl citrate at concentrations above about 19%-yielded samples with improved oil resistance and flake resistance. The same trend was seen when incorporating above about 19% trimethyl pentaphenyl dimethicone. In comparison, commercial comparative examples (which utilize silicone resin technology) had inferior oil resistance properties.

Example 10

Two Plasticizer Sticks

The following invention and comparative examples were prepared and evaluated according to the protocols described in example 9. The results of the evaluation are provided in the table below.

TABLE 5

| Ingredient Name | Comparative Example 10 A | Comparative Example 10 B | Comparative Example 10 C | Invention Example 10 D | Comparative Example 10 E |
|---|---|---|---|---|---|
| Oil Dispersion Example 3 | 51.02 49% oil dispersions solids 51% isododecane | 51.02 49% oil dispersions solids 51% isododecane | 51.02 49% oil dispersions solids 51% isododecane | 51.02 49% oil dispersions solids 51% isododecane | 51.02 49% oil dispersions solids 51% isododecane |
| Tributyl citrate | 0 | 1.39 | 3.125 | 8.33 | 5 |
| Trimethyl pentaphenyl dimethicone | 0 | 1.39 | 3.125 | 8.33 | 3.4 |
| Alcohol Wax | 1.25 | 1.25 | 1.25 | 1.25 | 1.25 |
| Polyethylene Wax | 13 | 13.00 | 13.00 | 13.00 | 13.00 |
| MICA | 3 | 3 | 3 | 3 | 3 |
| Pigment | 4.3 | 4.3 | 4.3 | 4.3 | 4.3 |
| Volatile Solvent | 27.43 | 24.65 | 22.18 | 10.77 | 19.07 |
| Ratio of plasticizers Tributyl citrate: trimethyl pentaphenyl trisiloxane | NA | 1:1 | 1:1 | 1:1 | 1:1.47 |
| Oil Dispersion Solids: Plasticizer | NA | 8.99:1 | 4:1 | 1.5:1 | 2.98:1 |
| Oil Resistance | 2 | 2 | 2 | 2 | 2 |
| Flake Testing | 3 | 3 | 3 | 1 | 3 |

| Ingredient Name | Invention Example 10 F | Invention Example 10 G |
|---|---|---|
| Oil Dispersion Example 3 | 51.02 49% oil dispersions solids 51% isododecane | 51.02 49% oil dispersions solids 51% isododecane |
| Tributyl citrate | 11.7 | 5 |
| Trimethyl pentphenyl dimethicone | 5 | 11.7 |
| Alcohol Wax | 1.25 | 1.25 |
| Polyethylene Wax | 13.00 | 13.00 |
| MICA | 3 | 3 |
| Pigment | 4.3 | 4.3 |
| Volatile Solvent | 10.75 | 10.75 |
| Ratio of Plasticizers Tributyl citrate: trimethyl pentaphenyl trisiloxane | 2.34:1 | 1:2.34 |
| Oil Dispersion: Plasticizer | 1.49:1 | 1.49:1 |
| Oil Resistance | 1 | 1 |
| Flake Testing | 1 | 1 |

Example 11

The following invention and comparative examples were prepared and evaluated according to the protocols described below. The results of the evaluation are provided in the table.

TABLE 6

| Ingredient Name | Invention Example 11 A |
|---|---|
| Oil Dispersion Example 3 | 53.420 46.8% oil dispersions solids 53.2% isododecane |
| Tributyl citrate | 5.00 |
| Trimethyl pentaphenyl dimethicone | 12.00 |
| Alcohol Wax | 1.25 |
| Polyethylene Wax | 13.00 |
| Pigment | 4.3 |
| Volatile Solvent | 7.77 |
| Ratio of plasticizers | |
| Tributyl citrate:trimethyl pentaphenyl trisiloxane | 1:2.40 |
| Oil Dispersion solids:Plasticizer | 1.47:1 |
| Oil Resistance | 1 |
| Flake Testing | 1 |

TABLE 7

| Ingredient Name | Invention Example 11 B |
|---|---|
| Oil Dispersion Example 3 | 53.420 |
|  | 46.8% oil dispersions solids |
|  | 53.2% isododecane |
| Tributyl citrate | 5.00 |
| Trimethyl pentaphenyl dimethicone | 12.00 |
| Alcohol Wax | 1.25 |
| Polyethylene Wax | 13.00 |
| Pigment | 3.28 |
| Pearls/Mica | 4.28 |
| Volatile Solvent | 7.77 |
| Ratio of plasticizers |  |
| Tributyl citrate:trimethyl pentaphenyl trisiloxane | 1:2.4 |
| Oil Dispersion:Plasticizer | 1.47:1 |

Samples containing blended plasticizers also gave some unique results. Samples with oil dispersions to plasticizer at 2:1 or greater amounts of plasticizer achieved the most improved oil resistance and flake resistance. In terms of plasticizer ratio to one another, within the oil dispersion: plasticizer ratio 2:1, the top performing samples ranged from 2.34:1 tributyl citrate to trimethyl pentaphenyl trisiloxane to 1:2.34 tributyl citrate to trimethyl pentaphenyl trisiloxane.

Example 12

In Vivo Assessment

Lipstick samples were evaluated in a study in which the subjects were blinded to the samples they were evaluating. The formula was applied on the subjects lips and allowed to set for five minutes. Following the five minute set time, subjects were asked to kiss a slab of bioksin. The transfer of the formula onto the bioskin was visually ranked relative to an Atlas for ranking. In terms the non-transfer score, inventive samples were found to be less transferring compared to both of the commercial comparative samples. The results of the evaluation are set forth below.

TABLE 8

| Sample | Sample Size | Non-transfer Score |
|---|---|---|
| Invention Example 11 B | 7 | 3.3(±1.4) |
| Commercial Comparative Example A - MQ/Dimethicone | 6 | 5.8(±0.4) |
| Commercial Comparative Example B - Polypropylsilsesquioxane | 6 | 5.7(±0.5)3 |

What is claimed is:

1. A cosmetic composition comprising:
   a dispersion of acrylic polymer particles that comprises particles of a C1-C4 alkyl (meth)acrylate polymer and at least one stabilizer selected from the group consisting of isobornyl (meth)acrylate homopolymers and statistical copolymers of isobornyl (meth)acrylate and of C1-C4 alkyl (meth)acrylate present in an isobornyl (meth)acrylate/C1-C4 alkyl (meth)acrylate weight ratio of greater than 4
   at least one volatile oil,
   an uncoated coloring agent,
   a thickening agent, and
   at least about 15% by weight with respect to the weight of the composition of at least one plasticizing agent.

2. The composition of claim 1, wherein the composition comprises at least two plasticizing agents.

3. The composition of claim 1, wherein the composition is solid.

4. The composition of claim 1, wherein the composition is liquid.

5. The composition of claim 1, in the form of an emulsion.

6. The composition of claim 1, wherein the composition is anhydrous.

7. The composition of claim 1, wherein the polymer of the particles is a methyl acrylate and/or ethyl acrylate polymer.

8. The composition of claim 1, wherein the polymer of the particles comprises an ethylenically unsaturated acid monomer or the anhydride thereof.

9. The composition of claim 8, wherein the polymer of the particles further comprises from 80% to 100% by weight of C1-C4 alkyl (meth)acrylate and from 0 to 20% by weight of ethylenically unsaturated acid monomer, relative to the total weight of the polymer.

10. The composition of claim 1, wherein the polymer of the particles is at least one selected from the group consisting of:
    methyl acrylate homopolymers;
    ethyl acrylate homopolymers;
    methyl acrylate/ethyl acrylate copolymers;
    methyl acrylate/ethyl acrylate/acrylic acid copolymers;
    methyl acrylate/ethyl acrylate/maleic anhydride copolymers;
    methyl acrylate/acrylic acid copolymers;
    ethyl acrylate/acrylic acid copolymers;
    methyl acrylate/maleic anhydride copolymers; and
    ethyl acrylate/maleic anhydride copolymers.

11. The composition of claim 1, wherein the polymer particles have an average size ranging from 100 nm to 250 nm.

12. The composition of claim 1, wherein the stabilizer is at least one selected from the group consisting of:
    isobornyl acrylate homopolymers;
    statistical copolymers of isobornyl acrylate/methyl acrylate;
    statistical copolymers of isobornyl acrylate/methyl acrylate/ethyl acrylate; and
    statistical copolymers of isobornyl methacrylate/methyl acrylate.

13. The composition of claim 1, wherein the at least one volatile oil is present in the composition is in an amount ranging from about 25 to about 54 percent by weight of the total weight of the composition.

14. The composition of claim 1, wherein at least one plasticizer is a plasticizer containing at least one ester group and at least one plasticizer is a plasticizer containing at least one phenyl group, wherein the weight ratio of plasticizer containing at least one ester group to plasticizer containing at least one phenyl group is from 2.5:1 to 1:2.5 and wherein the weight ratio of acrylic polymer particles to plasticizer is from 2:1 to 1:1.

15. The composition of claim 14, wherein the plasticizer containing at least one ester group is tributyl citrate and the plasticizer containing at least one phenyl group is pentaphenyl trimethicone.

16. The composition of claim 1, wherein the polymer of the particles comprises from 80% to 100% by weight of C1-C4 alkyl (meth)acrylate and from 0 to 20% by weight of ethylenically unsaturated acid monomer, relative to the total weight of the polymer,
    wherein the polymer particles have an average size ranging from 100 nm to 250 nm, wherein the stabilizer is at least one selected from the group consisting of isobornyl acrylate homopolymers; statistical copolymers of isobornyl acrylate/methyl acrylate; statistical copolymers of isobornyl acrylate/methyl acrylate/ethyl acrylate; and statistical copolymers of isobornyl methacrylate/methyl acrylate, wherein the at least one volatile oil is present in the composition is in an amount ranging from about 25 to about 54 percent by weight of the total weight of the composition, wherein at least one plasticizer is a plasticizer containing at least one ester group and at least one plasticizer is a plasticizer containing at least one phenyl group, wherein the weight ratio of plasticizer containing at least one ester group to plasticizer containing at least one phenyl group is from 2.5:1 to 1:2.5 and wherein the weight ratio of acrylic polymer particles to plasticizer is from 2:1 to 1:1.

* * * * *